(12) United States Patent
Vartiainen et al.

(10) Patent No.: US 10,322,035 B2
(45) Date of Patent: Jun. 18, 2019

(54) CONNECTOR RECEPTACLE WITH CONTACT SUPPORTS FOR MOISTURE SENSOR

(71) Applicant: SCA Hygiene Products AB, Göteborg (SE)

(72) Inventors: Kent Vartiainen, Lerum (SE); Sofia Hermansson, Västra Frölunda (SE); Per Ole Simenstad, Oslo (NO)

(73) Assignee: ESSITY HYGIENE AND HEALTH AKTIEBOLAG, Göteborg (DE)

( * ) Notice: Subject to any disclaimer, the term of this patent is extended or adjusted under 35 U.S.C. 154(b) by 739 days.

(21) Appl. No.: 14/787,294

(22) PCT Filed: Apr. 30, 2013

(86) PCT No.: PCT/EP2013/059049
§ 371 (c)(1),
(2) Date: Oct. 27, 2015

(87) PCT Pub. No.: WO2014/177205
PCT Pub. Date: Nov. 6, 2014

(65) Prior Publication Data
US 2016/0113822 A1   Apr. 28, 2016

(51) Int. Cl.
*A61F 13/42* (2006.01)
*H01R 43/16* (2006.01)
(Continued)

(52) U.S. Cl.
CPC ........... *A61F 13/42* (2013.01); *H01R 13/639* (2013.01); *H01R 13/6683* (2013.01);
(Continued)

(58) Field of Classification Search
CPC . A61F 13/42; A61F 2013/424; H01R 13/639; H01R 13/6683; H01R 43/16;
(Continued)

(56) References Cited

U.S. PATENT DOCUMENTS 2,858,515 A * 10/1958 Thunander ............. H01R 13/26
174/138 R
4,106,001 A * 8/1978 Mahoney ................ A61F 13/42
128/886
(Continued)

FOREIGN PATENT DOCUMENTS

CN        101238613 A      8/2008
DE         19937779 A1 *   2/2001   ............. A61F 13/42
(Continued)

OTHER PUBLICATIONS

First Chinese Office Action dated Feb. 12, 2018 issued in corresponding Chinese patent application No. 2013800761542 (10 pages) and its English-language translation thereof (9 pages).
(Continued)

*Primary Examiner* — Kathryn E Ditmer
(74) *Attorney, Agent, or Firm* — Drinker Biddle & Reath LLP (57) ABSTRACT

A receptacle is provided for connecting an electronics enclosure to an absorbent article having at least one sensor element. The receptacle includes: a base frame having a base surface; an enclosure retainer for retaining the enclosure relative to the base surface at an engagement position; and at least one contact support surface, oriented toward the engagement position, arranged to be displaceable away from the engagement position relative to the base surface and biased to protrude from the base surface toward the engagement position. An absorbent article and method of manufacture thereof and an absorbent article management system using the receptacle are also provided.

22 Claims, 7 Drawing Sheets

(51) Int. Cl.
*H01R 13/639* (2006.01)
*H01R 13/66* (2006.01)
*G01N 27/12* (2006.01)

(52) U.S. Cl.
CPC ........ *H01R 43/16* (2013.01); *A61F 2013/424* (2013.01); *G01N 27/121* (2013.01)

(58) Field of Classification Search
CPC .... G01N 27/121; A61B 5/202; A61B 5/6808; A61B 5/6879; A61B 5/688; A61B 5/6884; A61B 5/6892; G08B 21/00; G08B 21/20
See application file for complete search history.

(56) References Cited

U.S. PATENT DOCUMENTS

| | | | |
|---|---|---|---|
| 4,295,009 A * | 10/1981 | Weidler | H04R 17/00 310/324 |
| 5,392,032 A | 2/1995 | Kline et al. | |
| 5,469,146 A | 11/1995 | Gurler | |
| 5,557,263 A | 9/1996 | Fisher et al. | |
| 5,568,128 A | 10/1996 | Nair | |
| 5,813,117 A * | 9/1998 | Natali | H01R 13/245 29/622 |
| 6,563,065 B1 * | 5/2003 | Schrammek | H01H 1/34 200/249 |
| 7,250,547 B1 | 7/2007 | Hofmeister et al. | |
| 7,977,529 B2 | 7/2011 | Bergman et al. | |
| 2003/0011479 A1 | 1/2003 | Bluteau | |
| 2004/0064115 A1 | 4/2004 | Arora et al. | |
| 2004/0207530 A1 * | 10/2004 | Nielsen | A61F 13/42 340/604 |
| 2005/0156744 A1 | 7/2005 | Pires | |
| 2006/0270283 A1 * | 11/2006 | Kumazawa | G02B 6/3897 439/676 |
| 2007/0123089 A1 * | 5/2007 | Nishio | H01R 13/639 439/342 |
| 2007/0252711 A1 | 11/2007 | Long et al. | |
| 2008/0243099 A1 | 10/2008 | Tippey et al. | |
| 2009/0005748 A1 * | 1/2009 | Ales | A61F 13/42 604/361 |
| 2011/0095884 A1 * | 4/2011 | Xu | A61F 13/42 340/539.11 |
| 2011/0151708 A1 | 6/2011 | Kaneko et al. | |
| 2011/0263952 A1 | 10/2011 | Bergman et al. | |
| 2011/0295619 A1 | 12/2011 | Tough | |

FOREIGN PATENT DOCUMENTS

| | | | | |
|---|---|---|---|---|
| GB | 2354867 A * | 4/2001 | | A61F 13/42 |
| GB | 2354867 A | 4/2001 | | |
| JP | 2002-515975 | 5/2002 | | |
| JP | 2004-529730 | 9/2004 | | |
| RU | 2005 108 996 A | 9/2005 | | |
| WO | WO-96/14813 A1 | 5/1996 | | |
| WO | WO-97/42613 A2 | 11/1997 | | |
| WO | WO-00/00144 A2 | 1/2000 | | |
| WO | WO-02/101679 A1 | 12/2002 | | |
| WO | WO-2004/100763 A2 | 11/2004 | | |
| WO | WO-2006/047815 A1 | 5/2006 | | |
| WO | WO-2011/054045 A1 | 5/2011 | | |
| WO | WO-2011/156862 A1 | 12/2011 | | |
| WO | WO-2014/146693 A1 | 9/2014 | | |

OTHER PUBLICATIONS

English-language translation of a Russian Decision on Grant dated Jun. 7, 2017 issued in corresponding Russian patent application No. 2015150729 (5 pages).
European Office Action dated Apr. 25, 2017 issued in corresponding European patent application No. 13 721 645.3 (9 pages).
English-language translation of a Japanese Office Action dated Jan. 30, 2017 issued in corresponding Japanese patent application No. 2016-510946 (3 pages).
Second Chinese Office Action dated Oct. 16, 2018 issued in corresponding Chinese patent application No. 201380076154.2 (11 pages) and its English-language translation thereof (11 pages).

* cited by examiner

CONNECTOR RECEPTACLE WITH CONTACT SUPPORTS FOR MOISTURE SENSOR

CROSS-REFERENCE TO PRIOR APPLICATION

This application is a § 371 National Stage Application of PCT International Application No. PCT/EP2013/059049 filed Apr. 30, 2013, which is incorporated herein in its entirety.

TECHNICAL FIELD

The present disclosure relates to a receptacle for engagement with a corresponding electronics enclosure, for providing an absorbent article, such as a diaper, a sanitary towel, an incontinence garment, a medical dressing and the like, with sensing and/or data logging capabilities. Especially, the receptacle is suitable to be, or may be provided, attached to an absorbent article having sensors in order to enable easy connection of conductors of the sensors to contacts of the electronics enclosure.

TECHNICAL BACKGROUND

Absorbent articles, such as diapers, sanitary towels, incontinence garments, medical dressings and the like, have widespread utility in both domestic and institutional settings for such purposes as the care of infants, the management of menstrual discharge, the management of bodily efflux or exudate and the management of incontinence. However, a known problem associated with the use of absorbent articles is that the articles have a finite capacity for absorption which, if exceeded, will cause the absorbent article to become ineffective, e.g. to leak, or at least to fail to absorb further.

Therefore, users of such articles, or their carers, must predict when an absorbent article is nearing its absorbent capacity and must then take steps to replace the article before capacity is reached. In situations where there are many users of such absorbent articles but relatively fewer carers, such as in institutional settings, the management of the capacity of the various absorbent articles in use becomes a significant administrative burden.

Since absorbent articles are available in a variety of absorbent capacities, the user or carer must also determine, from those products which are available, which capacity of article to select. For example, in some circumstances it may be preferable to select an article of a lower capacity which is changed more frequently in contrast to an article of relatively larger capacity which is changed less frequently. Factors influencing this choice will be the nature of the absorption required, i.e. whether intermittent large quantities or a continuous smaller rate, as well as the total volume expected to be absorbed during a given period of time.

It can be very difficult for a user or carer to accurately predict or determine the state of an absorbent article, in terms both of utilised absorbent capacity and the need for the article to be replaced. Even where the absorbent demands on the article are reasonably predictable, a period of record-keeping and experimentation is required before a pattern may be established and appropriate absorbent articles provided.

Systems which are able to alert the user or carer to saturation or impending saturation of the absorbent article are therefore of benefit. Furthermore, systems which are able to monitor the usage pattern of a particular absorbent article, and of a series of absorbent articles associated with a particular individual, over a period of time, are of particular benefit.

Such systems may take the form of an absorbent article having embedded sensors which connect to a logger unit to monitor and record the sensor data over time. The sensors can, for example, be moisture sensors. When the absorbent capacity of the absorbent article is approached or exceeded, the user or the carer can be notified, on the basis of the recorded sensor data, that the absorbent article requires replacement.

Additionally, data obtained from a particular user over time can be used to monitor both the health of the user and the appropriateness of the absorbent article for that user over an extended period and can be used to provide better information for the care of the user. For example, an event, such as an incontinence event, leading to saturation of the article can be predicted and action, such as toileting action, taken before the event occurs.

Figure 7:
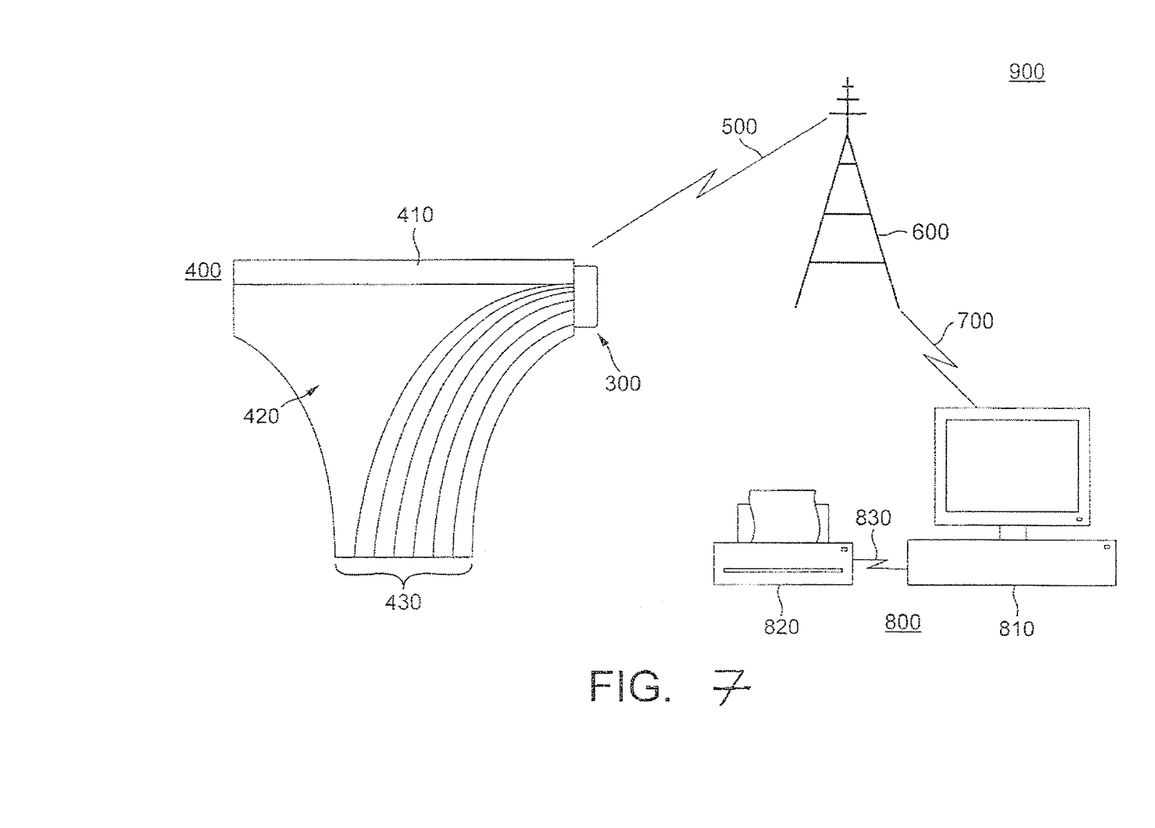
FIG. 7 is a system diagram illustrating an incontinence monitoring system in which the receptacle of the present disclosure may be employed.

One exemplary system is shown in FIG. 7, in which an absorbent article 400, exemplified here as a diaper and having a waistband 410 and an absorbent area 420, is provided with a logger unit 300 attached to the waistband 410 and having sense elements, in the form of sense wires 430, extending from the logger unit 300 running through the absorbent area. The sense wires 430 may be used to detect moisture, for example by detecting changes in the conductivity between the wires. The sense wires may be only partly exposed to the absorbent area, for example by providing insulation, to localise the region of sensing. The particular wiring pattern depicted is wholly exemplary, and will be selected according to the sensing requirements.

Figure 1:
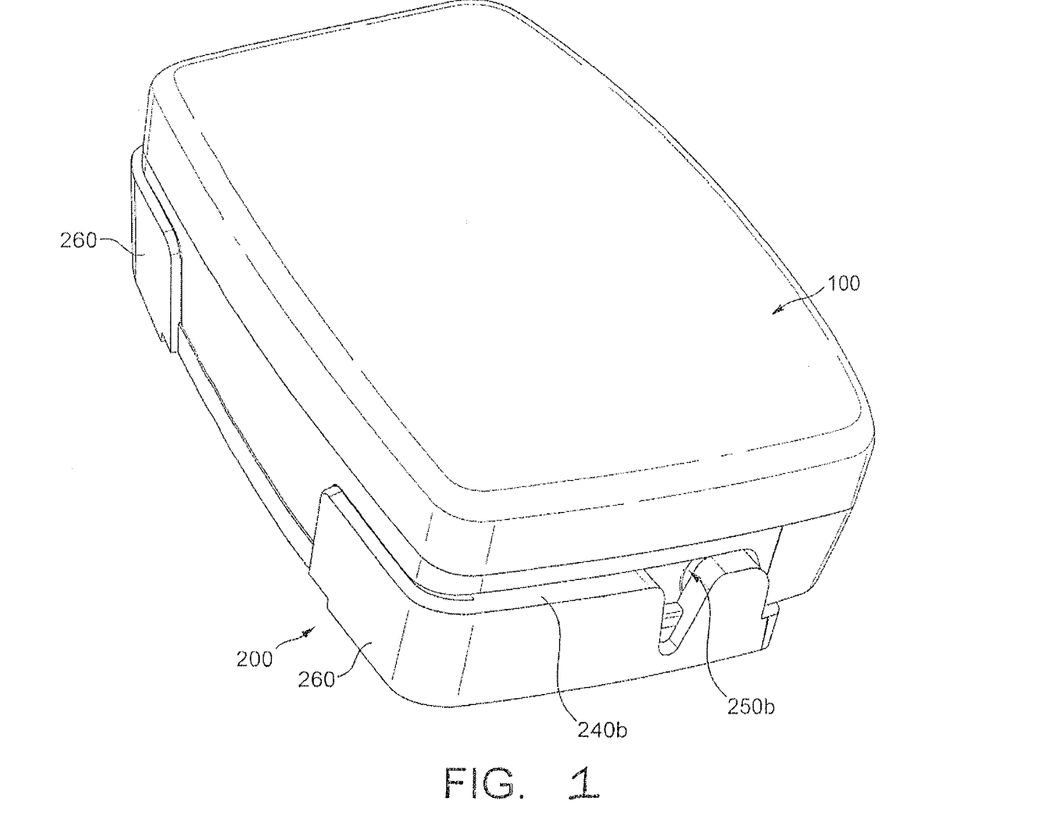
FIG. 1 shows an electronics enclosure in a state of engagement with a receptacle.

The logger unit 300, including data-logging electronics such as a power source, processor, memory, instruction store, data store, communications bus, and data link interface, which cooperate to store, process, and/or forward the data derived from sense wires, is connected by data link 500 to a data receiver 600. In the example of FIG. 1, data link 500 is a wireless data link, and data receiver 600 is a wireless data receiver. However, it is also possible that a docking functionality can be provided between the logger 300 and a docking station functioning as data receiver 600 to transfer data recorded in the logger 300 when the logger 300 is placed into the docking station. In a further alternative, data link 500 can be provided over the cellular telephone network, in which case data receiver 600 may be implemented as a cellular base station.

The data received at data receiver 600 is then transmitted by a further data link 700 to data processing equipment 800, exemplified as computer terminal 810 and output device 820 mutually connected by data link 830. Here, the computer terminal 810, which is an example of a general purpose data processing device, conducts processing on the sensor data received from the logger unit 300 via data links 500 and 700 and data receiver 600 and takes action based on the same, for example by outputting alerts, predictions, or statistics via output device 820. Here, the output device is shown as a line printer, but could, for example, be another form of hard copy printer, a visual display unit, a visual alarm panel, or an audio output device, without limitation.

Such a system may provide a powerful tool for the management of users of absorbent articles.

However, absorbent articles are conventionally disposable absorbent articles for reasons of hygiene and convenience. Although reusable absorbent articles are known, they are rarely used, especially in institutional and clinical settings, for reasons of economy and hygiene, amongst others.

Therefore, in the arrangement of FIG. 7, since the logger unit 300 is connected to sensor wires 430, which extend through the article 400, when the absorbent article 400 is to be discarded after a use, the logger unit 300 must be discarded also. However, the logger unit 300 is generally far more costly than the article 400 to manufacture. Thus, the system of FIG. 7 may be very expensive to operate, especially for an extended period of time. Further, the repeated disposal of electronic waste becomes environmentally unsound. Furthermore, discarding the logger 300 with the article 400 provides a data management challenge for the user, the carer or the institution, in assuring that when a new diaper with logger is provided to a user to replace a discarded diaper with logger, the logger is correctly initialised and data linking the logger to the user are correctly recorded.

The Applicant has developed a system, described in International patent application PCT/EP2013/055686, the contents of which are herein incorporated by reference to the extent permitted by law, of a co-operating receptacle and electronics enclosure in which the receptacle is provided to the absorbent article and the sensing or data logging electronics are provided to the enclosure. Such a system provides easy connection and disconnection of the enclosure from the receptacle when the absorbent article is changed.

However, when connecting a receptacle for an electronics enclosure to an absorbent article having sensor elements, there is a need to ensure that the sensor elements, or conductors extending therefrom, are easily positioned in the receptacle for electrical connection to corresponding contacts on the enclosure. Further, there is a need to ensure that electrical contacts on the enclosure are securely and reliably electrically connected to the sensor elements or conductors extending therefrom when an enclosure is engaged with a corresponding receptacle.

The present disclosure provides solutions to this problem.

SUMMARY

According to a first aspect, there is provided a receptacle for connecting an electronics enclosure to an absorbent article having at least one sensor element, the receptacle including: a base frame having a base surface; an enclosure retainer for retaining the enclosure relative to the base surface at an engagement position; and at least one contact support surface, oriented toward the engagement position, arranged to be displaceable away from the engagement position relative to the base surface and biased to protrude from the base surface toward the engagement position.

In some embodiments, the receptacle includes a tab or finger that extends from the base frame and that provides the contact support surface at a position on the tab member away from a junction between the tab and the base frame.

In some embodiments, the tab or finger is arranged to flex relative to the base surface.

In some embodiments, wherein the tab or finger includes a conductor guide for aligning a conductor relative to the contact support surface.

In some embodiments, the conductor guide includes a notch at an end of the tab or finger away from the junction between the tab and the base frame.

In some embodiments, wherein the base frame includes a base conductor guide at or near the junction between the tab and the base frame.

In some embodiments, wherein the base conductor guide includes a notch.

In some embodiments, the tab or finger extends from the base member in an engagement direction of the enclosure with the receptacle.

In some embodiments, the contact support surface is conductive.

In some embodiments, the receptacle includes guides for restricting an engagement direction of the enclosure with the receptacle.

In some embodiments, the base frame includes a conductor clamp for restricting movement relative to the base frame of a conductor extending to the contact support surface.

In some embodiments, the clamp includes a first frame portion and a second frame portion, the first frame portion having a first clamp surface, the second frame portion having a second clamp surface, the first and second frame portions being engageable to clamp a conductor extending to the contact support surface from between the first and second clamp surfaces.

In some embodiments, the first frame portion provides the enclosure retainer and the second frame portion provides the contact support surface.

In some embodiments, the second clamp surface faces the engagement position.

In some embodiments, one of the first and second clamp portions includes alignment projections and the other of the first and second clamp portions includes corresponding alignment apertures for relatively aligning the first and second frame portions prior to alignment.

In some embodiments, the first frame portion has a first ancillary clamp surface and the second frame portion has a second ancillary clamp surface, the first and second ancillary clamp surfaces being arranged to clamp a conductor extending from between the first and second clamp surfaces via the contact support surface.

In some embodiments, the first frame portion has an aperture, the second frame portion has an insert portion supporting the contact support surfaces, and the insert portion projects away from the first clamp surface to extend into the aperture when the first frame portion and the second frame portions are engaged.

In some embodiments, one of the insert and a rim of the aperture are provided with retaining clips and the other of the insert and the rim of the aperture are provided with retaining lips, the retaining clips and retaining lips being mutually configured to retain the insert within the aperture when the first frame portion and the second frame portion are engaged.

According to a second aspect, there is provided an absorbent article having sensor elements, the article including a receptacle according to the first aspect and at least one conductor electrically connected to a sensor element, the conductor being supported on the at least one contact support surface for contacting a corresponding contact on the enclosure when engaged with the receptacle.

According to a third aspect, there is provided an absorbent article according to the second aspect in combination with a logger unit having logger electronics enclosed in an enclosure adapted to cooperate with the receptacle to connect the logger electronics to the sensor elements when the enclosure is engaged with the receptacle.

According to a fourth aspect, there is provided an absorbent article management system including the combination according to the third aspect; and data processing equipment for processing data acquired from the sensor elements by the logger.

According to a fifth aspect, there is provided a method of manufacturing an absorbent article having at least one sensor element, the method including: providing a receptacle according to the first aspect; and supporting a conductor, which is electrically connected to a sensor element, with the contact support element.

BRIEF DESCRIPTION OF THE DRAWINGS

To better understand the present invention, and to show how the same may be put into effect, reference will be made, by way of example only, to the accompanying Drawings, in which.

DETAILED DESCRIPTION OF PARTICULAR EMBODIMENTS

Embodiments of the present invention will now be described with reference to the Figures.

The configuration of the absorbent article and monitoring system of the present disclosure can be similar to that disclosed in the arrangement of FIG. 7. However, logger unit 300 is provided in a multi-part form, such as a two-part form as shown in FIG. 1.

FIG. 1 shows enclosure 100 and corresponding receptacle 200. Enclosure 100 houses the electronics for monitoring the sensors 430, while receptacle 200 provides a point of attachment for the enclosure 100 for releasably attaching the enclosure 100 to the absorbent article 400. The electronics, here, may include a power source, processor, memory, instruction store, data store, communications bus, and data link interface, which cooperate to store, process, and/or forward the data derived from sensor wires. To facilitate this, the sensors 430 are arranged to terminate in electrical contacts 211 at a termination zone of receptacle 200, at which the sensor wires 430 are terminated at electrical contacts. Enclosure 100 is provided with corresponding contacts such that when enclosure 100 is engaged with receptacle 200, the contacts of receptacle 200 come into electrical contact with the contacts of enclosure 100. Thus, when engaged in the receptacle 200, electronics enclosure 100 is able to communicate with the sense wires 430.

The construction and function of the termination zone is described in more detail below.

Receptacle 200 and enclosure 100 also provide corresponding guide and engagement means, such that enclosure 100 may be easily introduced to and securely retained within receptacle 200. Features, described below, are also provided to enable the enclosure 100 to be released from the receptacle 200 by the user in a convenient manner, such as one-handedly. This is particularly important in institutional settings, since the user may not be compliant with the directions of the carer, and therefore it is advantageous for the enclosure 100 to be as easy as possible to correctly engage with and be released from the receptacle 200, even without the user needing to look at the receptacle or the enclosure. Allowing one-handed engagement and disengagement permits the other hand of the carer to be free to perform other tasks, for example in record-keeping or in encouraging user compliance.

To achieve the engaged configuration, the enclosure 100 is appropriately oriented and aligned with the receptacle 200 and is then translated in an engagement direction towards the receptacle until engagement is achieved, resulting in an engaged configuration. Various features of both the enclosure 100 and the receptacle 200 cooperate to permit such an engagement process, and its reverse disengagement process, to be both convenient and reliable, as more fully described in PCT/EP2013/055686, referred to above.

Figure 2:
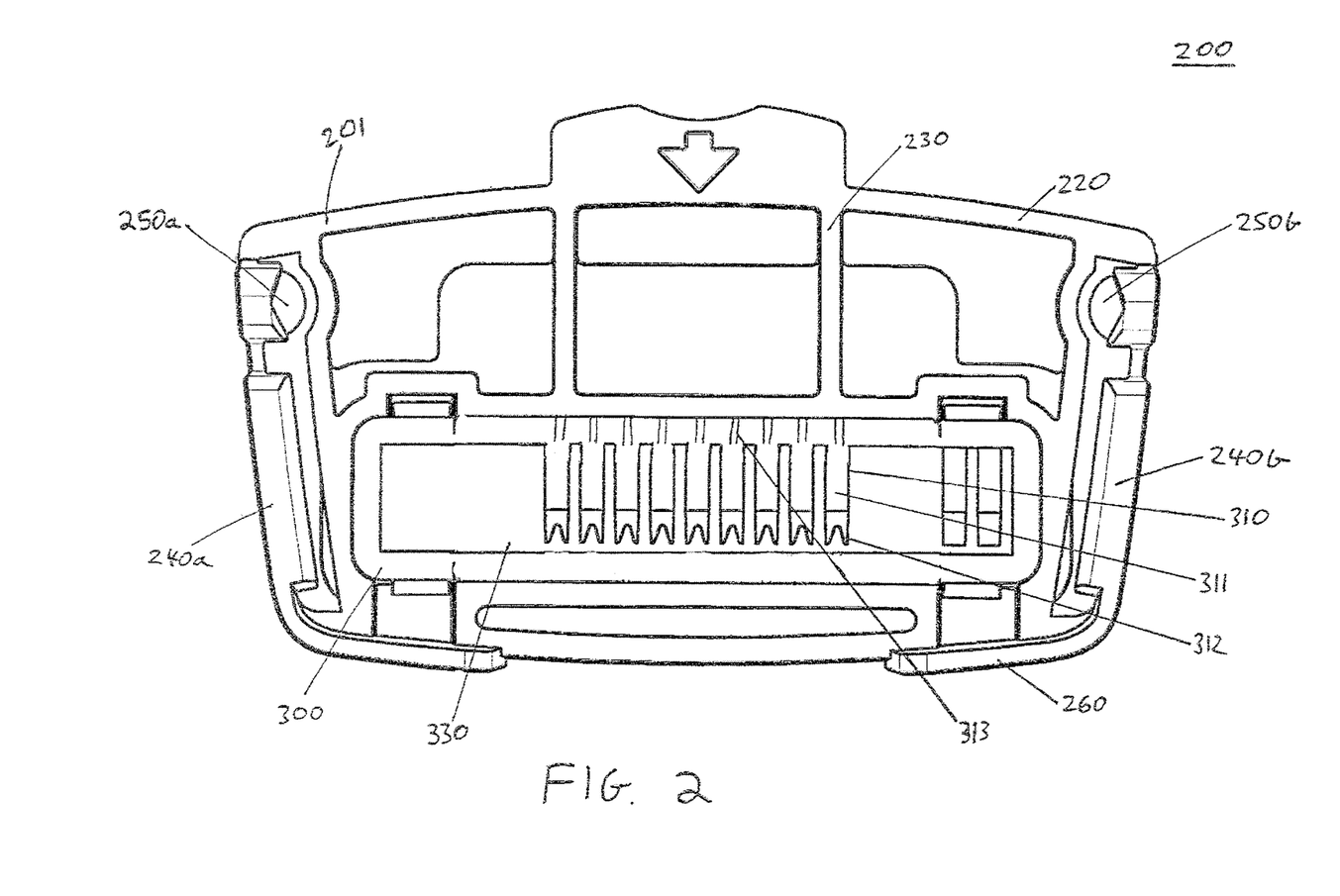
FIG. 2 shows a top view of a receptacle.

FIG. 2 shows the receptacle 200 from above. Receptacle 200 has a base surface 220 along which a surface of the enclosure 100 can translate in the engagement direction to achieve an engaged configuration. The base surface 220 defines a plane in which the engagement direction lies, and during the engagement process constrains the position of the enclosure relative to the receptacle 200 to motion in that plane, hereinafter termed the engagement plane. The base surface can be planar and continuous, although in the arrangement of FIG. 2 the base surface is defined by the upper surface of ribs 230, between which are depressed areas to reduce the mass of the receptacle 200 and to provide a region to act as the termination zone. Ribs 230 extend upwards from an essentially flat plate defining a lower absorbent-article-facing surface of the receptacle. However, in other configurations, different configurations of base surface, such as a planar continuous base surface, are possible.

The lower surface of the receptacle, in the present embodiment the opposite side of the flat plate to the base surface, is here suitable to be provided with an adhesive patch to enable the receptacle to be fixedly attached to a surface of the absorbent article. This is, however, purely exemplary, and other fixing means such as hook-and-eye fasteners or holes for threads or rivets may be contemplated to attach the receptacle to the absorbent article. When an adhesive patch is used to fix the receptacle to the absorbent article, the receptacle may be provided with the adhesive patch for fixing the receptacle to the absorbent article at the time of manufacture, for example by applying an adhesive patch with an absorbent-article-facing surface covered by release paper, or the adhesive may be applied subsequently, at the point at which the receptacle is provided to the absorbent article, for example as a spray or liquid.

Figure 3:
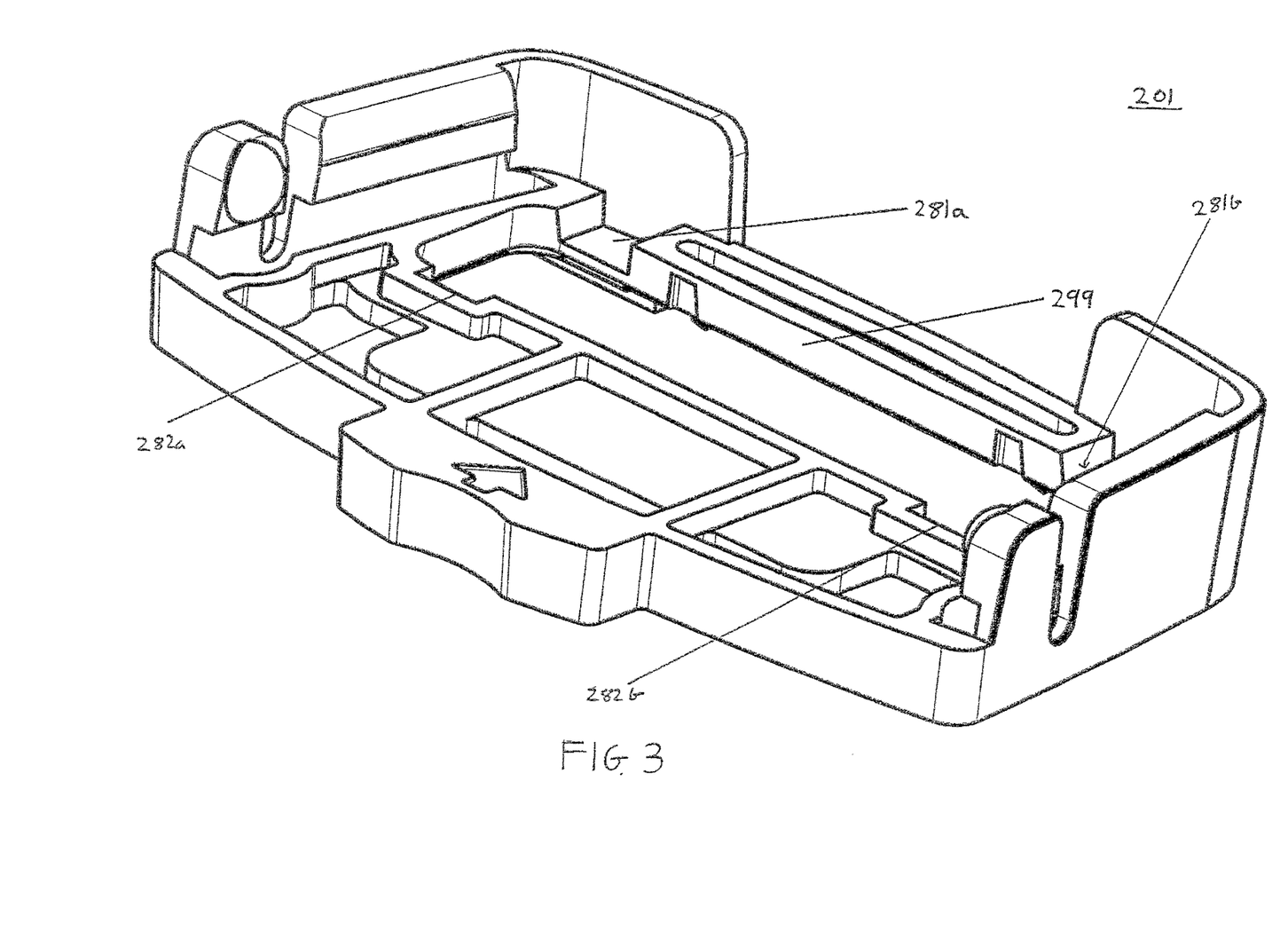
FIG. 3 shows a rear three-quarter view of a first base frame portion of a receptacle.

The receptacle 200 is also provided with features which enable the motion of the enclosure 100 relative to the receptacle 200 within the engagement plane to be restricted further. Particularly, receptacle 200 has guide rails 240a, 240b, extending inwardly from side walls of the receptacle in a plane parallel to the engagement plane on opposite sides of the base plane. These rails 240a, 240b, as most clearly may be seen in FIG. 3, are raised above the base plane in a direction perpendicular to the base plane, supported by the side walls, and are arranged to cooperate with corresponding guide grooves in the enclosure 100. The provision of guide rails 240a, 240b restricts rotation about the engagement direction, rotation about directions perpendicular to the engagement direction, as well as translation in the plane perpendicular to the engagement plane. The use of guide grooves and rails also permits initial misalignment, especially with regard to rotation of the enclosure 100 about an axis in the engagement plane but perpendicular to the engagement direction, to be smoothly corrected as the enclosure 100 and the receptacle 200 are brought into engagement. This is especially advantageous for enabling one-handed engagement, as the smooth correction of the direction of travel to the engagement direction is communicated to the carer as a gentle reorientation of the enclosure, as it is moved, into an orientation suitable for secure engagement.

The guide rails 240a and 240b are inclined relative to each other while remaining parallel to the engagement plane. Specifically, they are inclined such that they tend to converge in the engagement direction, such that the guide rails 240a, 240b are closer together at each of their ends which are more advanced in the engagement direction and the opposite ends of rails 240a, 240b, which are positioned rearwardly in the engagement direction, are relatively more separated. An effect of this relative inclination is that the guiding effect of the rails is progressively applied, such that an initial slight misalignment does not prevent engagement with the rails, but that as the enclosure 100 and the receptacle 200 are brought together into engagement, the guiding effect of the rails progressively increases to ensure that correct alignment is achieved during the more critical final phases of engagement.

The receptacle 200 is also provided with locking protrusions 250a, 250b, which are arranged to engage with corresponding depressions formed on the enclosure 100. In the present embodiment, the protrusions 250a, 250b are formed in the manner of an extension of rails 240a, 240b in the direction opposite to the engagement direction and separated from the rails by a small spacing. The protrusions 250a, 250b are elevated above the base surface 220 in a direction perpendicular to the base surface by respective resilient portions, formed as portions of the side walls of the receptacle, which enable each locking protrusion to flex inwardly and outwardly in a plane perpendicular to the engagement plane. Such a configuration reduces stress in the receptacle 200 and permits the locking protrusions 250a, 250b to snap into engagement with the corresponding locking depressions once engagement is reached. The snap locking action indicates in a tactile manner to the carer that secure engagement, and thus adequate electrical connection between the contacts, is achieved, and also acts as a deterrent to further forward motion in the engagement direction.

Receptacle 200 also has a forward barrier 260 at a forward edge of the base surface 220 in the engagement direction, in the form of wall 260 extending upwardly from the base surface in a direction perpendicular to the engagement plane. In the present embodiment, wall 260 is integrally formed with the side walls bearing rails 240a, 240b. This wall 260 acts as a further stop on further forward movement of the enclosure 100 in the receptacle 200 once the engagement position has been reached, if the snap locking action of the locking protrusions 250a, 250b into the depressions is disregarded. Wall 260 also provides a barrier against external force being inadvertently applied to the enclosure 100 in a direction opposite to the engagement direction, i.e. a disengagement direction, causing the enclosure to become disengaged.

Of course, there are many aspects of receptacle 200 which are optional, or which may be varied depending on need. For example, wall 260 may be absent, if it is not feared that the receptacle and the enclosure are likely to be subject to disengaging forces while in use. The guides 240b and 240a need not be relatively inclined, if it can be assumed that the user is able to align the enclosure and the receptacle appropriately for engagement. Indeed, guide rails 240a, 240b can be absent, and locking protrusions 250a, 250b and base surface 220 can alone be relied upon to guide the enclosure in the engagement plane. Alternatively, locking protrusions 250a, 250b can be absent, can be provided elsewhere, or can be replaced by other engagement means, e.g., catches or clips. The locking protrusions 250a, 250b could alternatively be provided on base surface 220 or on a surface opposed to base surface 220, thereby to form an enclosed receptacle on at least four sides. However, the described arrangement is considered advantageous in allowing the protrusions to perform an initial guiding function which facilitates one-handed operation.

Indeed, if a second surface positioned above base surface and oriented substantially parallel to the engagement plane were provided, guide rails 240a and 240b, as well as the walls supporting them, could be omitted, as this surface could then be used to guide the enclosure 100 into proper engagement with receptacle 200. Alternatively, rather than having locking protrusions 250a, 250b, locking depressions can be provided for corresponding locking protrusions on the enclosure. In some cases, it is preferred that the depressions or protrusions are provided forwardly of guide rails 240a, 240b, if present, in the engagement direction, rather than being positioned rearwardly as the locking protrusions 250a, 250b. Either configuration may be designed such that the locking effect is achieved only once the final, stable, engagement position is obtained.

Rails 240a, 240b need not be relatively inclined, although such inclination is presently considered advantageous. Indeed, base surface 220 need not be planar, but could be curved upwardly or downwardly in cross-section, looking along the engagement plane in the engagement direction. Such a surface will still restrict motion to an engagement plane, providing that a co-operating lower surface is provided to the enclosure. All such variants are considered to be within the scope of the present disclosure.

Enclosure 100 is provided with electrical contacts on a lower surface which, in the engaged configuration, is arranged so as to face base surface 220 of receptacle 200 when enclosure 100 is engaged with receptacle 200. In some embodiments, such contacts are flush with the lower surface. In other embodiments, such contacts slightly protrude from that surface. In yet further embodiments, such contacts are slightly recessed. In embodiments of the present disclosure, the termination zone of receptacle 200 is provided with contact support surfaces 311 which are oriented so as to be directed toward the lower surface of the enclosure 100 and which are displaceable away from the lower surface of enclosure 100 relative to base surface 220. The contact support surfaces 311 are biased to protrude from the base surface 220 towards the lower surface of electronics enclosure 100 so that conductive elements positioned on the contact support surfaces are urged into electrical connection with the contacts of the enclosure.

In the embodiment shown in FIG. 2, the receptacle 200 has a base frame 201, which provides, among other elements, the guide rails 240a, 240b, the locking protrusions 250a, 250b, the wall 260, and the base surface 220. The base frame thus defines an engagement space in which enclosure 100 may be accommodated. In the embodiment of FIG. 2, contact support surfaces 311 are provided as upper surfaces of fingers 310 which extend from the base frame to protrude above the base frame into the engagement space. The fingers extend in an engagement direction of the enclosure with the receptacle and are sufficiently thin so as to flex downward with force applied perpendicular to the base surface, providing by their flexure a countervailing bias force. Therefore, as the enclosure 100 slides along base surface 220 to the engagement position, contact between the contact support surfaces 311 and the lower surface of the enclosure 100 will tend to deflect the fingers toward the base surface.

In the embodiment of FIG. 2, the fingers extend from an inner wall of a depression or recess 330 formed in base surface 220 within the termination zone, so that as fingers 310 flex downwards, at least a portion of each finger is able to enter the depression. This allows fingers 310 to flex so that the contact support surfaces 311 are substantially co-planar with base surface 220. Accordingly, a conductor positioned on a contact support surface 311 may be urged into, and maintained in, electrical contact with a corresponding contact formed on the lower surface of the enclosure, as the enclosure slides into the receptacle along the engagement direction.

In some embodiments, it is not essential that each contact support surface be displaceable so as to be co-planar with the base surface. Depending on the geometry of the enclosure, it may be sufficient that the contact support surfaces 311 are displaceable toward the base surface but remain substantially above it even in an engaged configuration, without limitation.

By providing the contact support surfaces on the upper surfaces of projecting fingers, as shown in FIG. 2, the force required to engage the enclosure with the receptacle is small. However, depending on requirements, alternative configurations are possible. For example, rather than providing a plurality of fingers 310, which are longer in their projection direction than they are wide across their projection direction, a single tab may be provided, which is shorter in its projection direction than it is wide across its projection direction. In such a configuration, several conductors may be arranged on the contact support surface of the tab. However, although such a configuration may be easier to manufacture, it is less tolerant to deviations in the positions of the contacts on enclosure 100 from a common plane. Furthermore, removing material between positions at which conductors are intended to be located to form plural fingers rather than a single common tab improves flexibility of the fingers relative to the tab, and therefore reduces the required engagement force between the receptacle and the enclosure.

In the embodiment of FIG. 2, each finger 310 has, at an end away from the junction between the finger and the base frame (distal end) a notch 312. By providing such a notch, an elongate conductor, such as a conductive thread or wire, may be constrained to lie in a defined position relative to the distal end of the finger 310. Thus, the notch functions as a conductor guide. Especially, when the conductor lies along the contact support surface from the junction of finger 310 with the base frame to the distal end of finger 310, and beyond, and when tension is applied to the conductor while in situ, the biasing force of finger 310 away from base surface 220 will tend to retain the conductor in the notch 312, thereby maintaining the conductor at a relatively consistent position on contact support surface 311.

Also as shown in FIG. 2, a further conductor guide 313 is provided to the base surface at or near the position where the finger 310 joins the base frame, such that an elongate conductor may be guided, by co-operation of conductor guide 313 and conductor guide 312, to lie along the projection direction of finger 310. In the embodiment of FIG. 2, the conductor guide 313 is provided as a notch, but could also be provided, for example, as a pair of posts between which the conductor may be guided.

Figure 4:
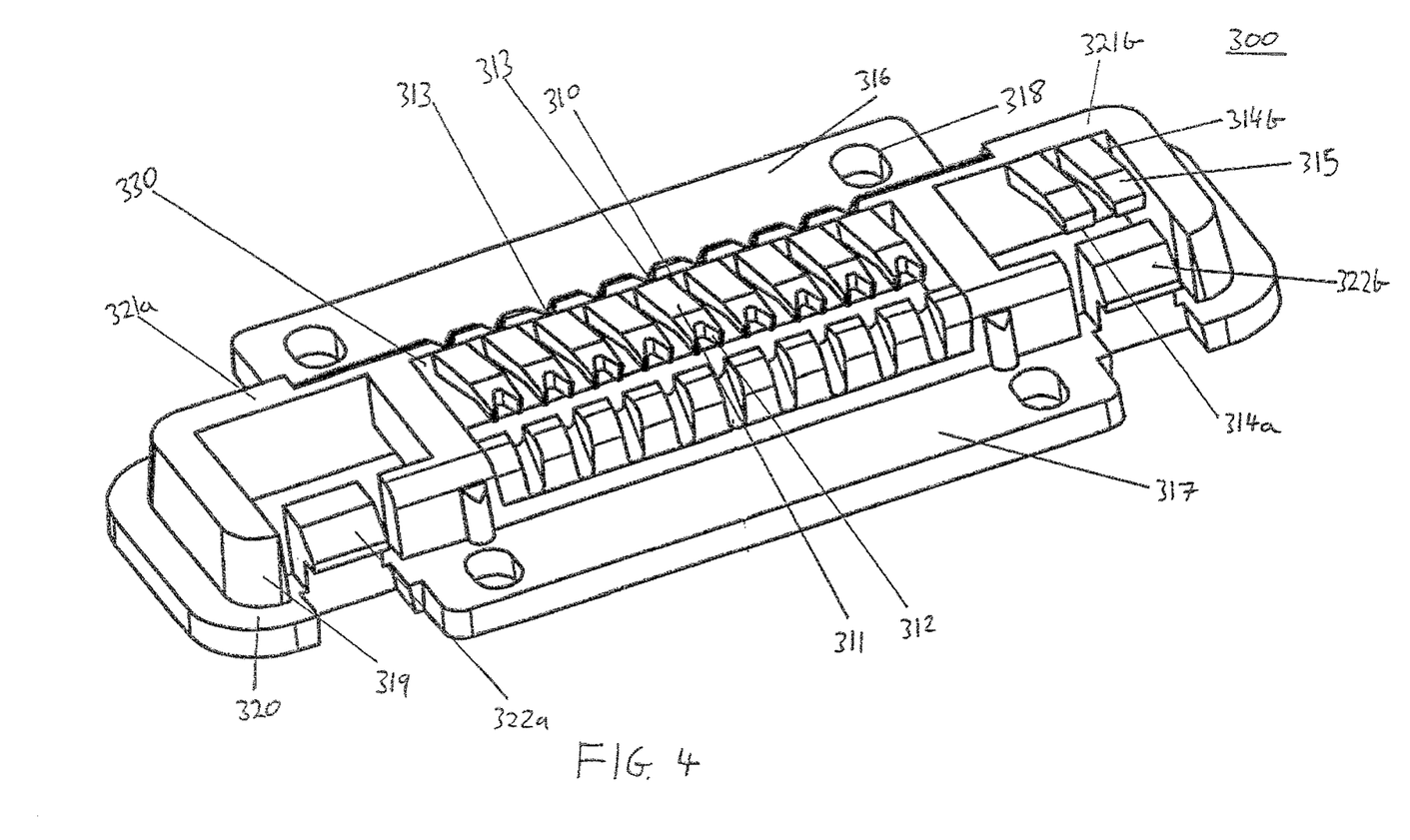
FIG. 4 shows a second base frame portion of a receptacle.

In one embodiment, the receptacle may have a two-part construction, comprising a first frame portion 201 as shown in FIG. 3 and a second frame portion 300 shown in FIG. 4.

First frame portion 201, shown in FIG. 3, provides the base surface 220, the locking projections 250a and 250b, and the guide rails 240a and 240b, i.e., those elements which enable the enclosure 100 to be securely engaged with the receptacle 200, while the second frame portion 300 provides, among others, the contact support surfaces 311 and associated fingers 310, as well as conductor guides 312 and 313.

In the arrangement of FIG. 3, first frame portion 201 includes an aperture 299 as the termination zone in base surface 220. The aperture is sized to permit an insert portion 319 of second frame portion 300 shown in FIG. 4 to be closely accommodated within aperture 299 to achieve the configuration shown in FIG. 2 by insertion of insert portion 319 from a lower, article-facing surface of receptacle 200 which is opposite to base surface 220. Such a configuration permits a conductor running along the absorbent article to run along the lower surface of first frame portion 201 and then to be presented above base surface 220 for a portion of its length, without being exposed at other locations on the enclosure-facing surfaces of receptacle 200. Such a configuration is able to prevent interference with or damage to the conductor when the enclosure is not engaged with the receptacle, since the conductor is only presented at the position where it is required to make contact with a corresponding contact of the enclosure.

In the arrangement of FIG. 4, the second frame portion 300 has retaining clips 322a, 322b and 321a, 321b, which engage with corresponding retaining lips 282a, 282b, 281a, 281b, provided on first frame portion 201 at the periphery of aperture 299 and shown in FIG. 3 to enable the second frame portion 300 to be inserted and then snap-fitted into the first frame portion 201 from below. In particular embodiments, each clip has portions of material removed from either side of the projection of the clip to enable the clip to flex independently of the remainder of the insert.

In the particular embodiment shown in FIG. 4, insert portion 319 projects from a flat peripheral portion 320 such that an upper surface of insert portion 319 surrounding recess 330 is substantially co-planar with base surface 220 when peripheral portion 320 abuts a lower surface of first frame portion 201. Furthermore, retaining clips 321a, 321b, 322a, 322b, and co-operating retaining lips 281a, 281b, 282a, 282b shown in FIG. 3, are mutually positioned and configured to be in locking engagement when peripheral portion 320 of second frame portion 300 abuts the lower surface of first frame portion 201.

Figure 6:
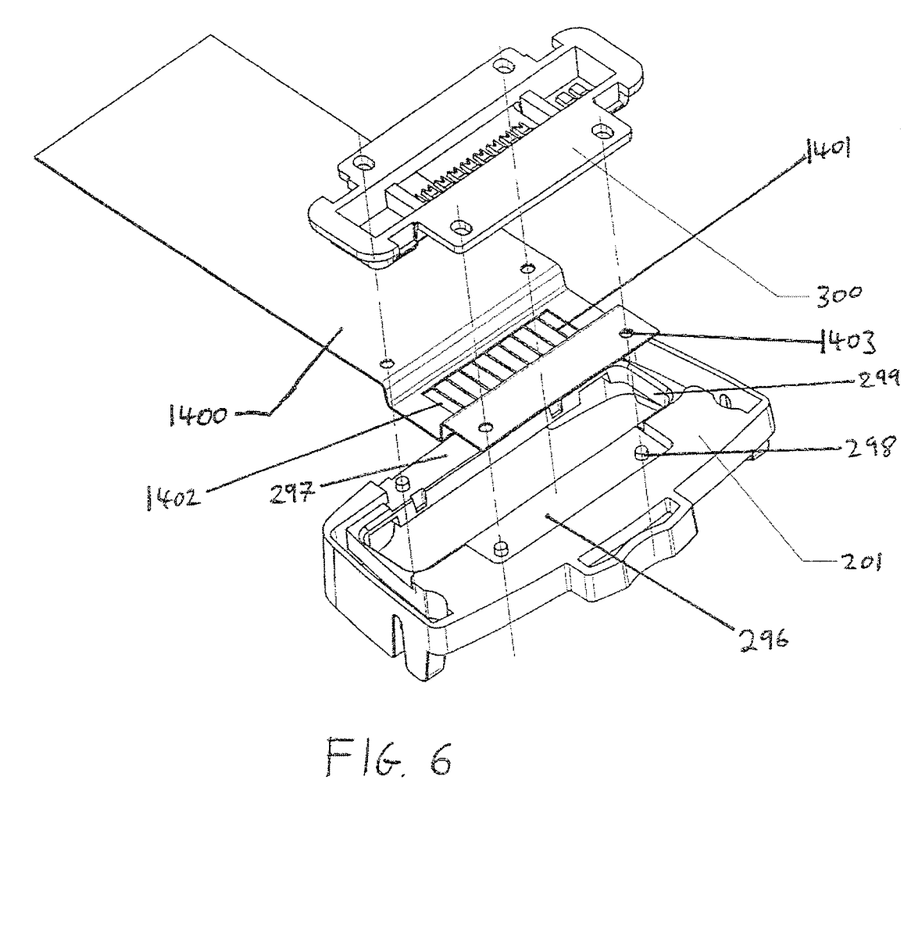
FIG. 6 is an exploded diagram of a receptacle, showing how a connector tail having exposed conductors may be positioned in the receptacle.

In the embodiment of FIG. 4, peripheral portion 320 of second frame portion 300 provides a clamp surface 316, which co-operates with clamp surface 296, shown in FIG. 6, formed on the lower surface of first base frame portion 201 to clamp, and thereby to restrict movement, of conductors passing between the clamp surfaces when the second frame portion 300 is engaged with the first frame portion 201. The clamp surface 316 is formed on the same side of contact support surface 211 as the junction of finger 310 with the second frame portion 300. Accordingly, conductors which run along lower surface of first frame portion 201 before passing between clamp surfaces 296 and 316 and then being presented on contact support surfaces 311 are secured against longitudinal and lateral displacement by co-operating clamping surfaces 296 and 316. In such a configuration, tab conductor guide 312 functions to restrain the conductor at the distal end of finger 310. Notably, although clamping surfaces 296 and 316 are illustrated as being flat, they may also be formed with channels extending from the periphery of the second frame portion 300 toward the contact support surfaces to accommodate individual conductors.

Also, an ancillary clamp surface 317 is formed on peripheral portion 320 of second frame portion 300 beyond the distal ends of fingers 310, to co-operate with an ancillary clamp surface 297, shown in FIG. 6, formed on the lower surface of first frame portion 201 and thus to restrain, by clamping, conductors running between clamp surfaces 316 and 296, along contact support surface 311, passing between conductor guides 313 and 312, and extending at least partially between ancillary clamp surfaces 297 and 317. Again, although clamping surfaces 297 and 317 are illustrated as being flat, they may also be formed with channels extending from the periphery of the second frame portion 300 toward the contact support surfaces to accommodate individual conductors.

In the illustrated configuration, clamp surface 316 and ancillary clamp surface 317 lie on opposite sides of contact support surfaces 311 in the length direction of fingers 310. With this configuration, a conductor lying along the length of contact support surface 311, from conductor guide 313 to conductor guide 312, and extending beyond the conductor guides may be clamped at portions of the conductor lying at either side of the contact support surface 311. Accordingly, not only may movement of the conductor be restricted on both sides of depression or recess 330, tension may also be provided along the portion of the conductor lying along the contact support surface to retain the conductor securely within guides 312 and 313.

As a result of such a construction, it is easy to secure conductors relative to contact support surfaces 311 by i) positioning conductors to run across clamp surface 316, through conductor guide 313, along contact support surface 311, through conductor guide 312, and along ancillary clamp surface 317 and ii) engaging the second frame portion 300 with first frame portion 201 by lowering first frame portion 201 onto second frame portion 300 until retaining clips 321a, 321b, 322a, 322b, engage with corresponding retaining lips 281a, 281b, 282a, 282b.

Figure 5:
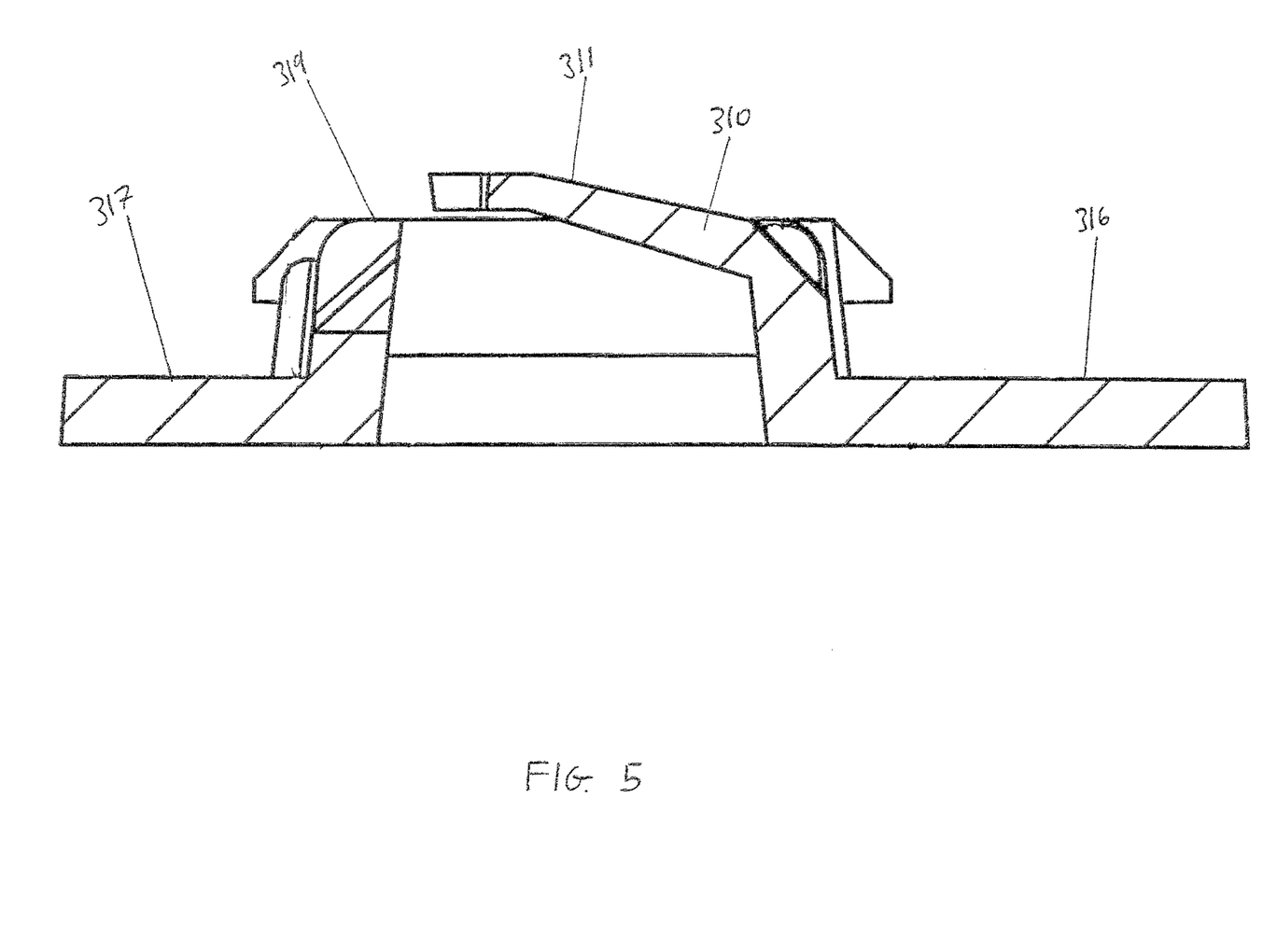
FIG. 5 shows a transverse section along a finger of the second base frame portion of FIG. 4.

Since the fingers 310 are provided on insert portion 319 of second frame portion 300, which rises above ancillary clamp surface 317 and clamp surface 316, shown in cross-section in FIG. 5, the relative approximation of first frame portion 201 and second frame portion 300 with conductors lying between tends to apply tension along the length of a conductor running along contact surface 311.

As shown in FIG. 4, second frame portion 300 is provided with alignment apertures 318, shown on clamp surface 316 and ancillary clamp surface 317, which are sized and positioned to co-operate with corresponding alignment projections 298, shown in FIG. 6, formed on clamp surface 296 and ancillary clamp surface 297. Alignment apertures 318 are slightly enlarged compared with alignment projections 298 in order to provide a degree of tolerance against any slight deviation from maintenance of the clamp surfaces of the second frame portion 300 parallel to the clamp surfaces of the first frame portion 201 during approximation and engagement of the first and second frame portions. Alternatively, the projections or could be provided to the first frame portion and the apertures to the second frame portion. In other arrangements, guide projections on a peripheral surface of second frame portion 300 could be arranged to co-operate with guide grooves on the inner walls of aperture 299, or vice versa.

In some configurations, as shown in FIG. 6, it is possible for conductors 1401, each of which is intended to lie along a contact support surface 311, to be provided in a laminate tail 1400. In such a configuration, conductors connected to sensor elements in the absorbent article are brought together in a laminate structure, either lying on, or sandwiched between two layers of, insulating, flexible sheet and running parallel to each other. The laminate tail protects the conductors from abrasion or deformation, prevents shorting between individual conductors, and arranges the conductors in a defined spacing for easy connection with the receptacle. In one configuration, the laminate tail 1400 may terminate in individual conductors 1401 projecting beyond an end of the tail. However, as shown in FIG. 6, it is possible to provide a window 1402 in a portion of laminate tail 1400 intermediate between the edges of the laminate tail and spaced from one end of the tail in order to expose a portion of conductors 1401 for arrangement on contact support surfaces 311.

In the arrangement of FIG. 6, a first portion of the laminate tail 1400 on one side of window 1402 in the length direction of laminate tail 1400 is clamped between clamp surfaces 296 and 316 while a second portion of the laminate tail 1400 on one side of window 1402 in the length direction of laminate tail 1400 is clamped between clamp surfaces 297 and 317. Accordingly, an exposed portion of each of conductors 1401 in window 1402 lies along a contact support surface 311 of each of fingers 310.

With such an arrangement, special care does not need to be taken to arrange the individual conductors relative to the individual fingers 310. Rather, since the conductors 1401 are already in a correct arrangement and spacing within window 1402, it is sufficient that window 1402 is correctly aligned with second frame portion 300 before first frame portion 201 is engaged with the second frame portion. To assist in this alignment, tail alignment apertures 1403 may be provided on laminate tail 1400 at positions to correspond to alignment projections 298. Thereby, alignment of the apertures 1403 with projections 298 ensures that conductors 1401 are correctly positioned to lie along contact support surfaces 311 and in conductor guides 312 and 313.

In the arrangement of FIG. 6, the laminate tail 1400 extends from a front surface of the receptacle to the sensor elements; it is also possible for the laminate to extend from a rear surface, as desired. Regardless of orientation, by providing such a configuration, it is possible to provide a receptacle which is easy to assemble to corresponding conductors, and with which an appropriately configured enclosure may easily be engaged to sit in secure engagement with the receptacle and good electrical contact with the conductors. However, to achieve these advantages, other configurations are also possible.

Considering the arrangement of FIGS. 2 and 3, it is also possible to provide the contact support surfaces as supported by individual springs or resilient elements located in aperture 299.

Furthermore, although the arrangement of FIG. 2 has guide rails 240a and 240b to constrain an engagement direction of the enclosure with the receptacle to lie in same plane as the base surface, alternatives are possible. For example, by omitting guide rails 240a and 240b, a vertical engagement direction, perpendicular to base surface 220, may be achieved. Alternatively, vertically-oriented guide rails, or guide rails extending at some other angle to the base surface, may be provided.

Additionally, although locking projections 250a and 250b are shown as inwardly-projecting protrusions to engage with corresponding depressions on enclosure 100, alternative means of engagement of the enclosure with the receptacle are possible. For example, the enclosure may be retained in the receptacle by catches, clips, magnets or adhesives.

Further, although, in the arrangement of FIGS. 4 and 5, the conductors are clamped at portions either side of the contact support surfaces 311, alternative means of securing the conductors relative to the contact support surfaces are possible. For example, each conductor may be formed with a beaded or knotted portion at an end distant from the sense elements, which portion may be hooked into conductor guides 312 and tension applied from the sense element end to retain the knotted or beaded portion of the conductor in the conductor guide. Such tension may be applied along the length of finger 310 by using clamp surface 316, without the necessity of providing ancillary clamp surface 317. Alternatively, conductors may be adhered to contact support surfaces 311, or may be embedded in contact support surfaces 311. A further alternative is to provide a conductive portion on contact support surface 311, for example by plating, adhering a foil, or applying a conductive paint, to which the conductors extending from the sensor elements may be bonded in a conductive manner, for example by using conductive paint or by soldering.

In the present disclosure, not every finger 310 need be associated with a conductor. For example, as shown in FIG. 4, two additional fingers 314a, 314b are provided, which are not configured with conductor guides to support conductors. In the embodiment of FIG. 4, these fingers have contact support surfaces coated with metallic paint, which contact support surfaces are mutually electrically connected via a further, bridging portion of conductive paint. The contact support surfaces of fingers 314a, 314b are arranged to contact corresponding connect/disconnect sense contacts of enclosure 100. By detecting a short circuit between the connect/disconnect contacts, electronics within the enclosure may determine whether or not the enclosure is securely engaged with receptacle 200 and that good electrical contact between the contacts of the enclosure and the conductors of the receptacle has been achieved.

The receptacle may be formed by any appropriate method known in the art, including injection moulding, vacuum forming, and subtractive machining. In particular embodiments, injection moulding in ABS plastic is used.

According to the present disclosure, as exemplified in the above embodiments, it is possible to provide a receptacle which is of low profile, which is easy to engage with conductors, and which is able to provide good electrical contact between the conductors and contacts of a corresponding enclosure.

In particular, the receptacle is suitable for provision to an absorbent article having sense elements, and to be provided in co-operation with an enclosure having data logging or sensing electronics to form part of a continence management system as shown in FIG. 7.

Particularly, the receptacle 200, which is relatively inexpensive and contains no electronics, may be provided as multiple instances to a series of diapers for use by one individual, while, in contrast to the system of FIG. 1, only one enclosure 100 is required, which is associated with a particular individual. During manufacture of each diaper 400, each receptacle 200 is attached at a convenient location and sense wires 430 are supported, via a laminate tail, on contact support surfaces of receptacle 200.

Enclosure 100, on the other hand, encloses data-logging electronics such as a power source, processor, memory, instruction store, data store, communications bus, and data link interface, which cooperate to store, process, and/or forward the data derived from sense wires 430 via data link 500, data receiver 600, data link 700, to data processing equipment 800. Where the data link 500 is a wireless data link, such transmission can be immediate and on-demand, or delayed and batch transmitted to save power or communication costs. Where data receiver is a docking station, the logger electronics will typically store data for a time period before downloading it through the docking station.

Initially, a user is fitted with absorbent article 400 to which receptacle 200 is provided, and enclosure 100 containing the logger electronics is engaged with the receptacle. The contacts of receptacle and enclosure are thus brought into electrical connection, and the electronics in the enclosure are able to access the sense wires for logging purposes.

When it becomes apparent that the absorbent article should be replaced, the enclosure containing the logger electronics is easily removed by the carer or the user by means of the disengagement process previously described, the absorbent article is discarded, and a replacement absorbent article, with a replacement receptacle 200, is provided. The enclosure 100 containing the logger electronics associated with a particular user is then engaged with the new receptacle 200, according to the previously-described engagement process, and is connected thereby to the sense wires 430 of the new absorbent article 400. Therefore, data logging can continue with a single logger while the relatively inexpensive absorbent articles are used and discarded.

Therefore, a system of monitoring the status of an absorbent article associated with a user, and of monitoring the status even of several different absorbent articles associated with that user over time, becomes cost effective and convenient.

Such a system may find application in residential homes, medical facilities, child care facilities, schools, corrective facilities, and other environments where the monitoring of the continence status of one individual or a plurality of individuals is required.

The foregoing embodiments and their variants have been disclosed for illustrative purposes only, and further variation is wholly possible within the capabilities of the skilled reader. Accordingly, the appended claims are intended to cover all modifications, substitutions, alterations, omissions and additions which one skilled in the art could achieve from the foregoing disclosure, taking into account his own general and specialist knowledge and expertise.

The invention claimed is:

1. A receptacle for connecting an electronics enclosure to an absorbent article having at least one sensor element, the receptacle comprising:
   a first frame portion comprising:
      a base surface; and
      an enclosure retainer for retaining the enclosure in contact with the base surface at an, engagement position; and
   a second frame portion releasably connected to the first frame portion and comprising:
      at least one contact support surface for supporting a conductor of the sensor thereon, oriented toward the engagement position, arranged to be displaceable away from the engagement position relative to the base surface and biased to protrude relative to the base surface toward the engagement position.

2. The receptacle according to claim 1, wherein the second frame portion of the receptacle comprises a tab or finger that extends from the second frame portion and that includes the at least one contact support surface at a position on the tab or finger away from a junction between the tab or finger and the second frame portion.

3. The receptacle according to claim 2, wherein the tab or finger is arranged to flex relative to the base surface.

4. The receptacle according to claim 2, wherein the tab or finger comprises the conductor guide for aligning a conductor relative to the at least one contact support surface.

5. The receptacle according to claim 2, wherein the second frame portion comprises a base conductor guide at or near the junction between the tab or finger and the second frame portion.

6. The receptacle according to claim 5, wherein the base conductor guide comprises a notch.

7. The receptacle according to claim 2, wherein the at least one contact support surface extends in a direction substantially parallel with the base surface.

8. The receptacle according to claim 1, wherein the at least one contact support surface is conductive.

9. The receptacle according to claim 1, wherein the receptacle comprises guides for restricting an engagement direction of the enclosure with the receptacle.

10. The receptacle according to claim 1, wherein a first frame peripheral portion of the first frame portion and a second frame peripheral portion of the second frame portion are engageable to clamp the conductor extending to the at least one contact support surface between the first frame peripheral portion and die second frame peripheral portion.

11. The receptacle according to claim 10, wherein a surface of the second frame peripheral portion contacting the conductor faces the engagement position.

12. The receptacle according to claim 11, wherein the first frame portion has an aperture, the second frame portion has an insert portion supporting the at least one contact support surface, and the insert portion projects away from a surface of the first flame peripheral portion contacting the conductor to extend into the aperture.

13. The receptacle according to claim 12, wherein one of the insert portion and a rim of the aperture are provided with retaining clips and the other of the insert portion and the rim of the aperture are provided with retaining lips, the retaining clips and retaining lips being mutually configured to retain the insert portion within the aperture.

14. The receptacle according to claim 10, wherein one of the first frame peripheral portion and the second frame peripheral portion comprises alignment projections and the other of the first frame peripheral portion and the second frame peripheral portion comprises corresponding alignment apertures for relatively aligning the first fame portion and, the second frame portion.

15. An absorbent article having sensor elements, comprising a receptacle according to claim 1 and at least one conductor electrically connected to a sensor element, the conductor being supported on the at least one contact support surface for contacting a corresponding contact on the enclosure when engaged with the receptacle.

16. A combination of an absorbent article according to claim 15 and a logger unit having logger electronics enclosed in an enclosure adapted to cooperate with the receptacle to connect the logger electronics to the sensor elements when the enclosure is engaged with the receptacle.

17. An absorbent article management system comprising:
the combination according to claim 16; and
data processing equipment for processing data acquired from the sensor elements by the logger.

18. A method of manufacturing an absorbent article having at least one sensor element, the method comprising:
providing a receptacle according to claim 1; and
supporting a conductor, which is electrically connected to a sensor element, with the at least one contact support surface.

19. A receptacle for connecting an electronics enclosure to an absorbent article having at least one sensor element, the receptacle comprising:
a base frame having a base surface;
an enclosure retainer for retaining the enclosure relative to the base surface at an engagement position; and
at least one contact support surface, oriented toward the engagement position, arranged to be displaceable away from the engagement position relative to the base surface and biased to protrude from the base surface toward the engagement position,
wherein the receptacle comprises a tab or finger that extends from the base frame and that includes the at least one contact support surface at a position on the tab or finger away from a junction between the tab or finger and the base frame,
wherein the tab or linger comprises a conductor guide for aligning a conductor relative to the contact support surface, and
wherein the conductor guide comprises a notch at an end of the tab or finger away from the junction between the tab or finger and the base frame.

20. The receptacle according to claim 19, wherein the base frame comprises a conductor clamp for restricting movement relative to the base frame of the conductor extending to the at least one contact support surface.

21. A receptacle for connecting an electronics enclosure to an absorbent article having at least one sensor element, the receptacle comprising:
base frame having a base surface;
an enclosure retainer for retaining the enclosure relative to the base surface at an engagement position; and
at least one contact support surface, oriented toward the engagement position, arranged to be displaceable away from the engagement position relative to the base surface and biased to protrude from the base surface toward the engagement position,
wherein the base frame comprises a conductor clamp for restricting movement relative to the base frame of a conductor extending to the at least one contact support surface,
wherein the clamp comprises a first frame portion and a second frame portion, the first frame portion having a first clamp surface, the second frame portion having a second clamp surface, the first and second frame portions being engageable to clamp the conductor extending to the at least one contact support surface between the first and second clamp surfaces, and
wherein the first frame portion has a first ancillary clamp surface and the second frame portion has a second ancillary clamp surface, the first and second ancillary clamp surfaces being arranged to clamp the conductor extending from between the first and second clamp surfaces via the at least one contact support surface.

22. The receptacle according to claim 21, wherein the first frame portion provides the enclosure retainer and the second frame portion provides the at least one contact support surface.

* * * * *